(12) United States Patent
Hannon et al.

(10) Patent No.: US 11,559,663 B2
(45) Date of Patent: Jan. 24, 2023

(54) CATHETER INCLUDING SLIDABLE PUSH GRIP

(71) Applicant: Medtronic Vascular, Inc., Santa Rosa, CA (US)

(72) Inventors: James Hannon, Galway (IE); Joanna Cunniffe, Galway (IE); Mick Donegan, Galway (IE); David Gannon, Galway (IE); Maria Larkin, Galway (IE); Francis Denis McEvoy, Laois (IE); Conor McNamara, Galway (IE); Barry O'Connell, Ardrahan (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 870 days.

(21) Appl. No.: 16/432,707

(22) Filed: Jun. 5, 2019

(65) Prior Publication Data

US 2019/0366049 A1    Dec. 5, 2019

Related U.S. Application Data

(60) Provisional application No. 62/680,844, filed on Jun. 5, 2018.

(51) Int. Cl.
    *A61M 25/01*      (2006.01)
    *A61M 39/02*      (2006.01)
    *A61M 25/00*      (2006.01)

(52) U.S. Cl.
    CPC .... *A61M 25/0136* (2013.01); *A61M 25/0105* (2013.01); *A61M 39/0247* (2013.01);
(Continued)

(58) Field of Classification Search
    CPC .......... A61M 25/0136; A61M 25/0105; A61B 2025/0059; A61B 2025/006
See application file for complete search history.

(56) References Cited

U.S. PATENT DOCUMENTS

| 4,665,918 A | * | 5/1987 | Garza | ....................... A61F 2/95 |
| | | | | 623/1.11 |
| 5,188,605 A | | 2/1993 | Sleep | |

(Continued)

FOREIGN PATENT DOCUMENTS

| CN | 103252014 B | 12/2016 |
| CN | 206491909 U | 9/2017 |

(Continued)

OTHER PUBLICATIONS

U.S. Appl. No. 16/432,679, filed Jun. 5, 2019.
(Continued)

*Primary Examiner* — Alexander J Orkin
(74) *Attorney, Agent, or Firm* — Shumaker & Sieffert, P.A.

(57) ABSTRACT

A catheter may include an elongate body extending from a proximal end to a distal end and defining a lumen; a push member mechanically coupled to the proximal end of the elongate body; and a slidable push grip disposed about an outer perimeter of the push member. The slidable push grip is controllably engageable with the push member. When the slidable push grip is in an engaged state with the push member, the slidable push grip transmits an axial force to the push member to enable the push member to transmit the axial force to the elongate body. When the slidable push grip is in a disengaged state with the push member, the slidable push grip is movable axially in at least one direction along a length of the push member while transmitting substantially no axial force to the push member.

22 Claims, 6 Drawing Sheets

(52) U.S. Cl.
CPC ............ *A61M 2025/006* (2013.01); *A61M 2025/0059* (2013.01); *A61M 2025/015* (2013.01); *A61M 2039/0205* (2013.01); *A61M 2039/0279* (2013.01); *A61M 2039/0282* (2013.01)

(56) References Cited

U.S. PATENT DOCUMENTS

| | | | |
|---|---|---|---|
| 5,527,292 A | 6/1996 | Adams et al. | |
| 5,658,309 A * | 8/1997 | Berthiaume | A61M 25/0097 606/192 |
| 5,868,755 A * | 2/1999 | Kanner | A61F 2/958 606/198 |
| 7,419,501 B2 | 9/2008 | Chiu et al. | |
| 7,736,355 B2 | 6/2010 | Itou et al. | |
| 8,133,267 B2 | 3/2012 | Leonhardt et al. | |
| 8,328,759 B2 | 12/2012 | Donawick | |
| 9,023,096 B2 | 5/2015 | Dwork | |
| 9,675,486 B2 | 6/2017 | Jimenez, Jr. et al. | |
| 2003/0050600 A1 * | 3/2003 | Ressemann | A61B 17/22 604/101.01 |
| 2007/0260219 A1 * | 11/2007 | Root | A61M 25/0069 604/523 |
| 2008/0051808 A1 | 2/2008 | Rivera et al. | |
| 2009/0024084 A1 * | 1/2009 | Khosla | A61M 25/0097 604/95.01 |
| 2009/0264865 A1 | 10/2009 | Kawai | |
| 2010/0030186 A1 * | 2/2010 | Stivland | A61M 25/09 604/528 |
| 2013/0237962 A1 | 9/2013 | Kawai | |
| 2014/0005647 A1 | 1/2014 | Shuffler et al. | |
| 2014/0012281 A1 | 1/2014 | Wang et al. | |
| 2014/0039461 A1 | 2/2014 | Anderson et al. | |
| 2014/0052097 A1 | 2/2014 | Petersen et al. | |
| 2014/0081243 A1 | 3/2014 | Zhou et al. | |
| 2014/0249508 A1 | 9/2014 | Wang et al. | |
| 2014/0276618 A1 | 9/2014 | Di Caprio et al. | |
| 2014/0283355 A1 | 9/2014 | Chin et al. | |
| 2016/0121086 A1 | 5/2016 | Castro et al. | |
| 2016/0296356 A1 | 10/2016 | Jordan et al. | |
| 2017/0189041 A1 | 7/2017 | Cox et al. | |
| 2017/0319232 A1 | 11/2017 | Kiev | |
| 2017/0354800 A1 | 12/2017 | O'Donovan | |
| 2019/0255299 A1 | 8/2019 | Fischell et al. | |

FOREIGN PATENT DOCUMENTS

| | | |
|---|---|---|
| EP | 0303487 A2 | 2/1989 |
| EP | 0808637 A2 | 11/1997 |
| GB | 2494905 A | 3/2013 |
| WO | 2003004085 A2 | 1/2003 |
| WO | 20100123371 A1 | 10/2010 |
| WO | 2017059186 A1 | 4/2017 |

OTHER PUBLICATIONS

U.S. Appl. No. 16/432,741, filed Jun. 5, 2019.
U.S. Appl. No. 16/432,763, filed Jun. 5, 2019.
Medtronic Launches Telescope(TM) Guide Extension Catheter to Support Complex Coronary Cases, https://finance.yahoo.com/news/medtronic-launches-telescope-tm-guide-133201972.html, May 16, 2019, 4 pp.
PCT/US2019/035645, The International Search Report and the Written Opinion, dated Sep. 24, 2019, 20pgs.
PCT/US2019/035648, The International Search Report and the Written Opinion, dated Sep. 24, 2019, 15pgs.
PCT/US2019/035634, The International Search Report and the Written Opinion, dated Sep. 24, 2019, 55pgs.
PCT/US2019/035637, The International Search Report and the Written Opinion, dated Sep. 30, 2019, 13pgs.

* cited by examiner

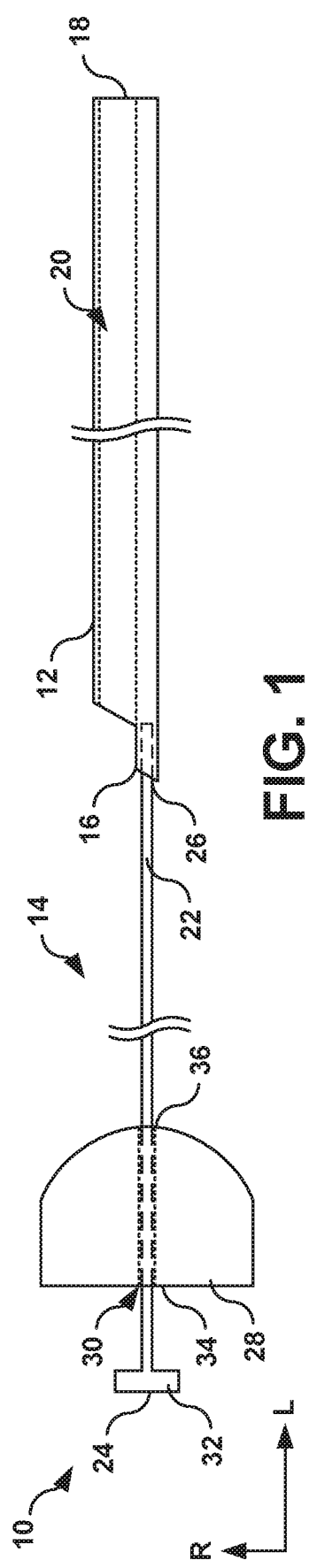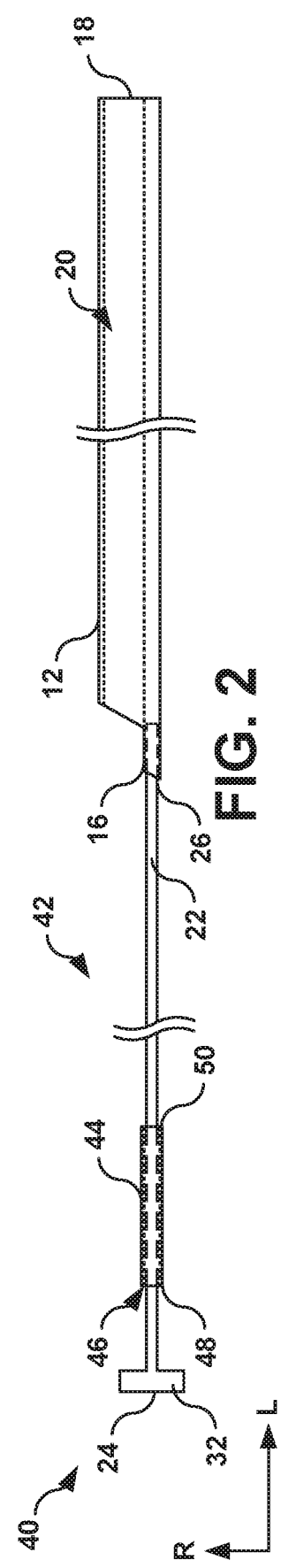

CATHETER INCLUDING SLIDABLE PUSH GRIP

This application claims the benefit of U.S. Provisional Application No. 62/680,844, filed Jun. 5, 2018, and entitled, "CATHETER INCLUDING SLIDABLE PUSH GRIP," the entire content of which is incorporated herein by reference.

TECHNICAL FIELD

This disclosure relates to medical devices including elongated members introducible to a body of a patient.

BACKGROUND

Medical catheters may be advanced into vasculature of a patient to provide a lumen through which a medical device or therapeutic agent may be introduced to a treatment site. Medical catheters may be advanced to the treatment site by a clinician applying an axial force to a portion of the catheter that is outside a body of the patient.

SUMMARY

This disclosure describes medical catheters that include a push assembly and an elongate body. The elongate body extends from a proximal end to a distal end and defines a lumen. The push assembly includes a push member and a slidable push grip. A distal end of the push member is mechanically coupled to a proximal end of the elongate body. The slidable push grip surrounds a perimeter of the push member and is controllably engageable with the push member. When disengaged from the push member, the slidable push grip may be slidable along a length of the push member. When engaged with the push member, the slidable push grip is substantially retained relative to the push member, such that forces applied to the slidable push grip are transmitted to the push member. In this way, the slidable push grip may facilitate application of axial forces to the push member, and, ultimately, the elongate body when the slidable push grip is engaged with the push member and may allow repositioning of the slidable push grip relative to the push member when the slidable push grip is disengaged from the push member. In some examples, the slidable push grip is not removable from the push member, such that in both the engaged and the disengaged states, the slidable push grip surrounds the perimeter of the push member.

Clause 1: A catheter comprising: an elongate body extending from a proximal end to a distal end and defining a lumen; a push member mechanically coupled to the proximal end of the elongate body; a slidable push grip disposed about an outer perimeter of the push member, wherein the slidable push grip is controllably engageable with the push member, wherein, when the slidable push grip is in an engaged state with the push member, the slidable push grip transmits an axial force to the push member to enable the push member to transmit the axial force to the elongate body, and wherein, when the slidable push grip is in a disengaged state with the push member, the slidable push grip is movable axially in at least one direction along a length of the push member while transmitting substantially no axial force to the push member.

Clause 2: The catheter of clause 1, wherein the push member comprises a proximal end stop at or near a proximal end of the push member, and wherein the proximal end stop is configured to prevent the slidable push grip from being removed off the proximal end of the push member.

Clause 3: The catheter of clause 1 or 2, wherein the slidable push grip surrounds the outer perimeter of the push member so the slidable push grip is not radially removable from the push member.

Clause 4: The catheter of any one of clauses 1 to 3, wherein the slidable push grip comprises at least one engagement feature configured to increase engagement with the push member on an inner surface of the slidable push grip.

Clause 5: The catheter of clause 4, wherein the at least one engagement feature comprises a coating applied to the inner surface of the slidable push grip, wherein the coating increases a coefficient of friction with the push member.

Clause 6: The catheter of clause 4, wherein the at least one engagement feature comprises a texture on the inner surface, wherein the texture increases a coefficient of friction with the push member.

Clause 7: The catheter of clause 4, wherein the at least one engagement feature comprises a geometric pattern formed in the inner surface.

Clause 8: The catheter of clause 7, wherein an outer surface of the push member comprises a complementary pattern.

Clause 9: The catheter of any one of clauses 1 to 8, wherein the slidable push grip further comprises a locking feature configured to controllably maintain the slidable push grip in the engaged state or the disengaged state.

Clause 10: The catheter of any one of clauses 1 to 9, further comprising a kink resistance sleeve disposed about the outer perimeter of the push member, wherein the kink resistance sleeve is configured to reduce radial bending or kinking of the push member.

Clause 11: The catheter of any one of clauses 1 to 10, further comprising a strain relief member attached to or integral with the slidable push grip and extending distally from a distal end of the slidable push grip.

Clause 12: The catheter of any one of clauses 1 to 11, wherein the slidable push grip is configured to default to the disengaged state and engage the push member in response to a radially inward force being applied to the slidable push grip.

Clause 13: The catheter of any one of clauses 1 to 12, wherein the slidable push grip is configured to default to the engaged state and disengage the push member in response to a radially inward force being applied to the slidable push grip.

Clause 14: A catheter system comprising: an outer catheter extending from an outer catheter proximal end to an outer catheter distal end and defining an outer catheter lumen; and a guide extension catheter (GEC) comprising the catheter of any one of clauses 1 to 13, wherein the guide extension catheter is configured to be received within the outer catheter lumen.

Clause 15: The catheter system of clause 14, wherein the elongate body of the guide extension catheter defines a maximum outer diameter that is less than a diameter of the outer catheter lumen.

Clause 16: The catheter system of clause 14 or 15, wherein the guide extension catheter defines a length that is greater than a length of the outer catheter.

Clause 17: A catheter comprising: an elongate body extending from a proximal end to a distal end and defining a lumen; a push member mechanically coupled to the proximal end of the elongate body, wherein the push member comprises a proximal end stop at or near a proximal end of the push member, and wherein the proximal end stop is configured to prevent the slidable push grip from being removed off the proximal end of the push member; a slidable push grip disposed about an outer perimeter of the push member, wherein the slidable push grip is controllably engageable with the push member, wherein, when the slidable push grip is in an engaged state with the push member, the slidable push grip transmits an axial force to the push member to enable the push member to transmit the axial force to the elongate body, and wherein, when the slidable push grip is in a disengaged state with the push member, the slidable push grip is movable axially in at least one direction along a length of the push member while transmitting substantially no axial force to the push member; a strain relief member attached to or integral with the slidable push grip and extending distally from a distal end of the slidable push grip; and a kink resistance sleeve separate from the slidable push grip and the strain relief member and disposed about the outer perimeter of the push member, wherein the kink resistance sleeve is configured to reduce radial bending or kinking of the push member.

Clause 18: The catheter of clause 17, wherein the slidable push grip comprises at least one engagement feature configured to increase engagement with the push member on an inner surface of the slidable push grip.

Clause 19: The catheter of clause 18, wherein the at least one engagement feature comprises a coating applied to the inner surface of the slidable push grip, wherein the coating increases a coefficient of friction with the push member.

Clause 20: The catheter of clause 18 or 19, wherein the at least one engagement feature comprises a texture on the inner surface, wherein the texture increases a coefficient of friction with the push member.

Clause 21: The catheter of any one of clauses 18 to 20, wherein the at least one engagement feature comprises a geometric pattern formed in the inner surface.

Clause 22: The catheter of clause 21, wherein an outer surface of the push member comprises a complementary pattern.

Clause 23: A method comprising: assembling a slidable push grip with a push member so the slidable push grip is disposed about an outer perimeter of the push member, wherein the slidable push grip is controllably engageable with the push member; and mechanically coupling a distal end of the push member to an elongate body of a catheter, wherein the elongate body extends from a proximal end to a distal end and defines a lumen, wherein, when the slidable push grip is in an engaged state with the push member, the slidable push grip transmits an axial force to the push member to enable the push member to transmit the axial force to the elongate body, and wherein, when the slidable push grip is in a disengaged state with the push member, the slidable push grip is movable axially along the length of the push member while transmitting substantially no axial force to the push member.

Clause 24: The method of clause 23, wherein the push member comprises a proximal end stop at or near a proximal end of the push member, and wherein the proximal end stop is configured to prevent the slidable push grip from being removed off the proximal end of the push member.

Clause 25: The method of clause 23 or 24, wherein the slidable push grip surrounds the outer perimeter of the push member so the slidable push grip is not radially removable from the push member.

Clause 26: The method of any one of clauses 23 to 25, further comprising forming at least one engagement feature configured to increase engagement with the push member in an inner surface of the slidable push grip.

Clause 27: The method of clause 26, wherein forming the at least one engagement feature comprises applying a coating to the inner surface of the slidable push grip, and wherein the coating increases a coefficient of friction with the push member.

Clause 28: The method of clause 26 or 27, wherein forming the at least one engagement feature comprises forming a texture on the inner surface, and wherein the texture increases a coefficient of friction with the push member.

Clause 29: The method of any one of clauses 26 to 28, wherein forming the at least one engagement feature comprises a forming geometric pattern in the inner surface.

Clause 30: The method of clause 29, further comprising forming a complementary pattern in an outer surface of the push member.

Clause 31: The method of any one of clauses 23 to 30, wherein the slidable push grip further comprises a locking feature configured to controllably maintain the slidable push grip in the engaged state or the disengaged state.

Clause 32: The method of any one of clauses 23 to 31, further comprising disposing a kink resistance sleeve about the outer perimeter of the push member, wherein the kink resistance sleeve is configured to reduce radial kinking of the push member.

Clause 33: The method of any one of clauses 23 to 32, further comprising attaching a strain relief member to the slidable push grip, wherein the strain relief member extends distally from a distal end of the slidable push grip.

Clause 34: The method of any one of clauses 23 to 32, further comprising forming a strain relief member as an integral part of the slidable push grip, wherein the strain relief member extends distally from a distal end of the slidable push grip.

Clause 35: The method of any one of clauses 23 to 34, wherein the slidable push grip is configured to default to the disengaged state and engage the push member in response to a radially inward force being applied to the slidable push grip.

Clause 36: The method of any one of clauses 23 to 35, wherein the slidable push grip is configured to default to the engaged state and disengage the push member in response to a radially inward force being applied to the slidable push grip.

Clause 37: A method comprising: introducing an outer catheter in vasculature of a patient, wherein the outer catheter extends from an outer catheter proximal end to an outer catheter distal end and defines an outer catheter lumen; introducing a guide extension catheter in the outer catheter lumen at the outer catheter proximal end, wherein the guide extension catheter comprises an elongate body extending from a proximal end to a distal end and defining a guide extension catheter lumen, a push member mechanically coupled to the proximal end, and a slidable push grip disposed about an outer perimeter of the push member, wherein the slidable push grip is controllably engageable with the push member, wherein, when the slidable push grip is in an engaged state with the push member, the slidable push grip transmits an axial force to the push member to enable the push member to transmit the axial force to the elongate body, and wherein, when the slidable push grip is in a disengaged state with the push member, the slidable push grip is movable axially in at least one direction along a length of the push member while transmitting substantially no axial force to the push member; while the slidable push grip is in the engaged state with the push member, applying a distal axial force to the slidable push grip to advance the guide extension catheter distally within the outer catheter lumen; disengaging the slidable push grip from the push member; repositioning the slidable push grip along the length of the push member; engaging the slidable push grip with the push member; and while the slidable push grip is in the engaged state with the push member, applying a distal axial force to the slidable push grip to further advance the guide extension catheter distally through the outer catheter lumen.

The details of one or more examples are set forth in the accompanying drawings and the description below. Other features, objects, and advantages will be apparent from the description and drawings, and from the claims.

BRIEF DESCRIPTION OF DRAWINGS

FIG. 1 is a conceptual side view illustrating an example catheter, which includes an elongate body and a push assembly including a push member and a slidable push grip.

FIG. 2 is a conceptual side view illustrating another example catheter, which includes an elongate body and a push assembly including a push member and a slidable push grip.

DETAILED DESCRIPTION

Figure 3:
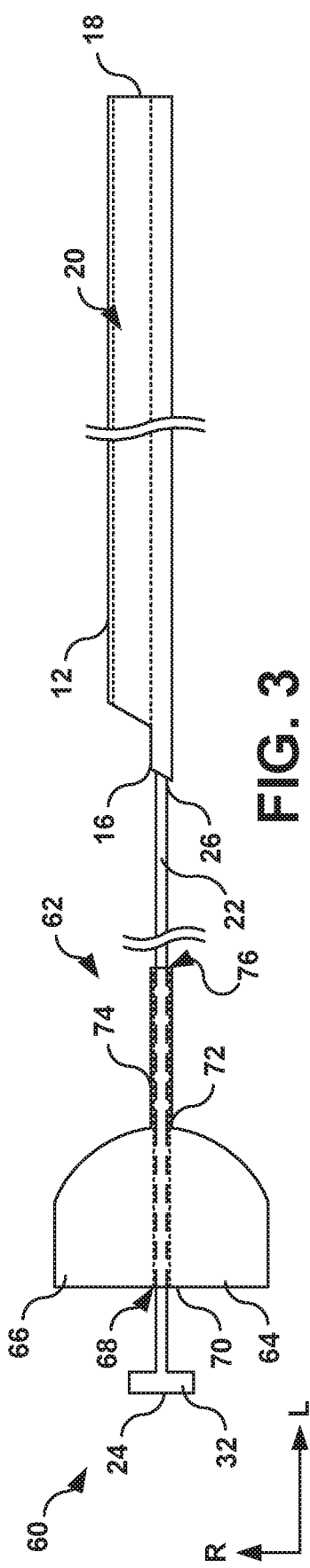
FIG. 3 is a conceptual side view illustrating an example catheter, which includes an elongate body and a push assembly including a push member and a slidable push grip that includes a strain relief member.

This disclosure describes medical catheters that include a push assembly and an elongate body. The elongate body extends from a proximal end to a distal end and defines at least one lumen, e.g., a longitudinal lumen that extends from at or near the proximal end to at or near the distal end of the elongate body. The at least one lumen may be sized to allow introduction of a medical device (e.g., a catheter, guidewire, filter, stent delivery system, and the like), therapeutic agent, or other element into vasculature or other tissue sites of a patient.

The push assembly includes a push member (also referred to as a shaft) and a slidable push grip. A distal end of the push member is mechanically coupled to the elongate body, e.g., to a proximal portion of the elongate body. The slidable push grip surrounds a perimeter of the push member and is controllably engageable with the push member. In some examples, the slidable push grip is not removable from the push member, such that in both an engaged state and a disengaged state, the slidable push grip surrounds the perimeter of the push member. Thus, in some examples, the slidable push grip may not be removable from around the push member in a radial direction (radially removable) or other direction transverse to a longitudinal axis of the push member.

When controlled to be disengaged from the push member (e.g., in the disengaged state), the slidable push grip may be slidable along a length of the push member. This enables the slidable push grip to move relatively freely along the length of the push member to be repositionable along the length of the push member. When engaged with the push member (e.g., in the engaged state), the slidable push grip is substantially retained relative to the push member, such that forces applied to the slidable push grip are transmitted to the push member. When the slidable push grip is substantially retained relative to the push member, the slidable push grip may not move relative to the push member or may move a small amount relative to the push member. In this way, the slidable push grip may facilitate controllable application of axial forces to the push member, and, ultimately, the elongate body, for example, to advance the elongate body through vasculature of a patient. The slidable push grip may allow a clinician to better grip the push member to apply selected forces, and may facilitate identification of the push member, e.g., in examples in which one or more other elongated medical devices, such as an outer catheter and a guidewire, are being used as part of the same therapeutic procedure. In some examples, the slidable push grip may enable a clinician to axially push the catheter using a single hand.

In some examples, the slidable push grip may include an integral strain relief member or be attached to a strain relief member. The strain relief member may extend distally from a distal end of the slidable push grip, e.g., in a direction towards the elongate body. The strain relief member may relieve or dissipate stress that otherwise would be concentrated in the push member at the distal end of the slidable push grip. Additionally, the strain relief member may provide radial stiffness to the push member to reduce or eliminate kinking of the push member in response to axial forces being applied to the slidable push grip when the slidable push grip is engaged with the push member.

In some examples, the push assembly may include a kink resistance sleeve. The kink resistance sleeve may be integral with, attached to, or separate from the slidable push grip. The kink resistance sleeve may provide radial stiffness to the push member to reduce or eliminate kinking of the push member in response to axial forces being applied to the slidable push grip when the slidable push grip is engaged with the push member. In some examples, a single component may act as both a strain relief member and a kink resistance sleeve and may be referred to as either a strain relief member or a kink resistance sleeve.

The medical catheters described herein may be used alone or in combination with an outer catheter. The outer catheter may extend from a proximal end to a distal end and define a catheter lumen, e.g., extending from at or near the proximal end to at or near the distal end. The outer catheter may be introduced in vasculature of a patient and advanced to near (but proximal to) a treatment site. The medical catheter described herein may define an outer diameter or cross-sectional area that is less than a diameter or cross-sectional area of the catheter lumen. The medical catheter may be inserted in the catheter lumen and advanced through the catheter lumen to a distal end of the outer catheter. The medical catheter described herein may be advanced distally out the distal end of the outer catheter until the entire or part of the elongate body extends past a distal end of the outer catheter, while the push assembly remains fully or partially within the lumen of the outer catheter. The push member has a lower profile than the elongate body, and, as a result, may occupy less space within the outer catheter lumen than the elongate body of the medical catheter. Thus, the push assembly may both facilitate pushability of the catheter through the outer catheter and/or through vasculature of a patient, while still enabling relatively large medical devices to be introduced through the outer catheter lumen to reach the lumen of the catheter. In this way, the medical catheters described herein may act as an extension catheter (also referred to herein as a guide extension catheter) for the outer catheter. In some examples, the medical catheters described herein may be used to traverse tortuous vasculature that the outer catheter is not sufficiently flexible to traverse or may be advanced through calcification within a body vessel that the outer catheter is not sufficiently low profile enough to traverse.

FIG. 1 is a conceptual side view of an example catheter 10, which includes an elongate body 12 and a push assembly 14. Elongate body 12 extends from a proximal end 16 to a distal end 18 and defines a lumen 20. In the example shown in FIG. 1, lumen 20 extends from at or near proximal end 16 to at or near distal end 18. Elongate body 12 may be formed from a suitable biocompatible polymer. In some examples, elongate body 12 includes multiple layers, such as an inner liner and an outer jacket, each of which may be formed from a suitable polymer.

In some examples, elongate body 12 may include at least one reinforcement element, such as a reinforcement coil or braid, which may extend for at least a portion of a length of elongate body 12 (length defined parallel to the L axis of the polar L-R axes shown in FIG. 1 for purposes of illustration only). The at least one reinforcement element may contribute to axial stiffness of elongate body 12 (e.g., stiffness along the length of elongate body 12) while allowing radial or transverse flexibility. The at least one reinforcement element may be formed using any suitable material, including, for example, relatively more stiff polymers, biocompatible metals or alloys, or the like.

In some examples, elongate body 12 may include different stiffness at different locations along elongate body 12. For example, a more proximal portion of elongate body 12 may be stiffer than a more distal portion of elongate body 12. In some examples, such a configuration may be achieved by including a reinforcement element that extends through the more proximal portion of elongate body 12 and does not extend to the more distal portion of elongate body 12, by changing the properties of the reinforcement member along the length of elongate body 12, by changing the materials from which elongate body 12 is formed, or any combination thereof. An elongate body 12 that includes a more proximal portion that is stiffer and a more distal portion that is more flexible may facilitate advancing of elongate body 12 through vasculature of a patient or an outer catheter, while allowing elongate body 12 to navigate tortuous portions of the vasculature.

In some examples, elongate body 12 includes at least one radiopaque marker which may be, for example, a radiopaque marker band (e.g., one or more partial or full rings) attached to elongate body 12, e.g., by an adhesive, by welding, by being embedded between different layers of elongate body 12, or another suitable technique. In some examples, the radiopaque marker may include tungsten, titanium, stainless steels, cobalt-chromium alloy, tantalum, or any other radiopaque material. The radiopaque marker may be positioned around an outer perimeter (e.g., an outer circumference) of elongate body 12 or may be encapsulated by elongate body 12. In some examples, elongate body 12 includes multiple radiopaque markers, e.g., one or more radiopaque markers near proximal end 16, one or more radiopaque markers near distal end 18, one or more markers intermediate proximal end 16 and distal end 18, or combinations thereof. The radiopaque markers may facilitate visualization of the catheter during a medical procedure to assist a clinician in positioning elongate body within vasculature of a patient. For example, elongate body 12 may include a radiopaque marker positioned to indicate a proximal opening to lumen 20 and/or to indicate a distal opening to lumen 20.

Push assembly 14 includes push member 22 and a slidable push grip, which in the example of FIG. 1, includes a slidable push tab 28. Push member 22 extends from a proximal end 24 to a distal end 26. Distal end 26 of push member 22 is mechanically coupled to elongate body 12 at or near proximal end 16. For example, distal end 26 of push member 22 may be embedded in the polymer from which elongate body 12 is at least partially formed (e.g., between an outer layer and inner layer of elongate body 12) or adhered to elongate body 12. In some examples, push member 22 is coupled to elongate body 12 such that distal end 26 of push member 22 is distal to proximal end 16 of elongate body 12.

Push member 22 is relatively stiff such that the push assembly 14 may be configured to facilitate introduction of catheter 10 in vasculature of a patient or an outer catheter. Push member 22 may be formed from any suitably stiff material, such as, for example, a biocompatible, relatively stiff polymer, a biocompatible, relatively stiff metal or alloy or the like. In some examples, push member 22 may be formed from a wire coated with a biocompatible polymer layer.

Push member 22 may define any suitable cross-sectional shape, and the cross-sectional shape of push member 22 may be substantially constant along the length of push member 22 or may change along the length of push member 22. For example, push member 22 may define a substantially circular or elliptical cross-section in a plane transverse to the longitudinal axis of push member 22.

Push member 22 extends to proximal end 24, at which an optional proximal end stop 32 may be present. Proximal end stop 32 may define a larger diameter or cross-sectional area (the cross-section being taken in a direction perpendicular to a longitudinal axis of push member 22) than push member 22 and may be configured to prevent slidable push tab 28 from being removed proximally from push member 22. For example, a diameter or cross-sectional area of proximal end stop 32 may be greater than a diameter or cross-sectional area of aperture 30 defined in slidable push tab 28. Proximal end stop 32 may be integral with or attached to proximal end 24 of push member 22. For example, proximal end stop 32 may be formed from the same material as push member 22 or may be formed from a different material and mechanically coupled to proximal end 24 of push member 22.

Push assembly 14 also includes slidable push tab 28. Slidable push tab 28 is disposed about an outer perimeter of push member 22. For example, as shown in FIG. 1, slidable push tab 28 may define an aperture 30 through which push member 22 extends. In this way, slidable push tab 28 may surround an outer perimeter or circumference of push member 22 such that slidable push tab 28 is not radially removable from push member 22 (e.g., removable in a direction parallel to the R-axis of FIG. 1).

Aperture 30 extends from a proximal end 34 to a distal end 36 of slidable push tab 28. Aperture 30 is sized to have a diameter or cross-sectional area slightly larger than the diameter or cross-sectional area of push member 22, which may enable slidable push tab 28 to slide along push member 22 in a direction corresponding to the L-axis direction in the example shown in FIG. 1.

In some examples, aperture 30 may not have a constant diameter or cross-sectional area along the length of aperture 30. For example, aperture 30 may define a reduced diameter or cross-sectional area at one or more locations. The reduced diameter or cross-sectional area may be substantially equal to the diameter or cross-sectional area of push member 22 such that slidable push tab 28 contacts push member 22 at this location. In this way, slidable push tab 28 may act as a movable hub that provides a fluid tight fitting between slidable push tab 28 and push member 22.

In accordance with some aspects of the disclosure, slidable push tab 28 is controllably engageable with push member 22. For example, a surface of slidable push tab 28 that defines aperture 30 may be controllably engageable with push member 22. As an example, slidable push tab 28 may be at least partially deformable such that a radially-inward force deforms at least the portion of slidable push tab 28 adjacent to aperture 30. In some such examples, removal of the radially-inward force may allow slidable push tab 28 to recover from the deformation and disengage from push member 22. In this way, slidable push tab 28 may be controlled between an engaged state and a disengaged state with respect to push member 22.

In the engaged state, slidable push tab 28 may be configured to transmit at least axial forces (parallel to the L-axis) applied to slidable push tab 28, e.g., by a clinician, to push member 22. In some examples, in the engaged state, slidable push tab 28 also may transmit radial or angular forces (parallel to the R-axis or about the L-axis, respectively) to push member 22, which may be, for example, rotational forces applied to push member 22 via slidable push tab 28. Slidable push tab 28 provides a surface for the clinician to grip, which may facilitate application of forces to push member 22 compared to directly gripping push member 22. Additionally or alternatively, slidable push tab 28 may facilitate identification of push member 22 by the clinician, e.g., in examples in which multiple wires or catheters are being introduced into vasculature as part of the same procedure.

In the disengaged state, slidable push tab 28 is configured to be movable axially along the length of push member 22 from proximal end stop 32 to proximal end 16 of elongate body 12. This enables a clinician to reposition slidable push tab 28 along push member 22, e.g., to select a new location (e.g., an axial location along a longitudinal axis of push member 22) for applying axial and/or radial forces to push member 22.

FIG. 1 illustrates one example configuration of slidable push grip. Slidable push grips may have other configurations, including other optional features. For example, FIG. 2 is a conceptual side view of another example catheter 40, which includes an elongate body 12 and a push assembly 42 including a push member 22 and a slidable push grip that includes a slidable push sleeve 44. Catheter 40 may be similar or substantially the same as catheter 10 of FIG. 1, aside from the differences described herein. For example, like catheter 10, catheter 40 includes elongate body 12, which extends from proximal end 16 to distal end and defines lumen 20. Catheter 40 also includes a push assembly 42, which, like catheter 10, includes a push member 22 that extends from proximal end 24 to distal end 26 and includes an optional proximal end stop 32. Distal end 26 of push member is mechanically coupled to elongate body 12 at or near proximal end 16.

Catheter 40 includes a slidable push sleeve 44. Slidable push sleeve 44 may surround a perimeter of push member 22. Slidable push sleeve 44 includes a body that extends from a slidable push sleeve proximal end 48 to a slidable push sleeve distal end 50. Slidable push sleeve 44 also defines an aperture 46 that extends from slidable push sleeve proximal end 48 to slidable push sleeve distal end 50. Aperture 46 is configured to receive push member 22, which is shown in FIG. 2 extending through aperture 46.

A diameter or cross-sectional area of aperture 46 is larger than an outer diameter or cross-sectional area of push member 22, such that push member 22 may slide through aperture 46. Like slidable push tab 28, slidable push sleeve 44 is controllably engageable with push member 22. For example, slidable push sleeve 44 may be formed from a polymer that is sufficiently flexible to allow slidable push sleeve 44 to deform in response to a compressive force applied by a clinician to a opposite sides of slidable push sleeve 44. When deformed by a sufficient force, the surface of slidable push sleeve 44 that defines aperture 46 may engage an outer perimeter of push member 22. Upon the force being removed, the surface of slidable push sleeve 44 that defines aperture 46 may disengage from the outer perimeter of push member 22. In this way, a clinician may change slidable push sleeve 44 from the disengaged state to an engaged state and vice versa by modulating an amount of radially inward force applied to slidable push sleeve 44.

Slidable push sleeve 44, as well as other slidable push tabs described herein, may include a visual or tactile indicator that enables a clinician to readily distinguish between slidable push sleeve 44 and other components, such as other catheters, a guidewire, or the like. For example, slidable push sleeve 44 may have a distinctive color or pattern on the external surface of slidable push sleeve 44 to allow easy visual identification of slidable push sleeve 44. As another example, slidable push sleeve 44 may have a distinctive texture defined in the external surface of slidable push sleeve 44 to allow easy tactile identification of slidable push sleeve 44. The texture may include, for example, a pseudorandom texture of a selected surface roughness; a knurled texture; a series of parallel or non-parallel ridges, grooves, or combinations thereof; or the like.

FIG. 3 is a conceptual side view of another example catheter 60, which includes elongate body 12 and a push assembly 62 including a push member 22 and a slidable push grip 64 that includes a strain relief member 74. Catheter 60 may be similar or substantially the same as catheter 10 of FIG. 1, aside from the differences described herein. For example, like catheter 10, catheter 60 includes elongate body 12, which extends from proximal end 16 to distal end and defines lumen 20. Catheter 60 also includes a push assembly 62, which, like catheter 10, includes a push member 22 that extends from proximal end 24 to distal end 26 and includes an optional proximal end stop 32. Distal end 26 of push member 22 is mechanically coupled to proximal end 16 of elongate body 12.

Push assembly 62 includes slidable push grip 64, which includes both a slidable push tab 66 and strain relief member 74. Slidable push tab 66 extends from a slidable push tab proximal end 70 to a slidable push tab distal end 72 and defines an aperture 68 extending from slidable push tab proximal end 70 to slidable push tab distal end 72. Slidable push tab 66 may be similar to or substantially the same as slidable push tab 28 of FIG. 1.

Strain relief member 74 extends from distally from slidable push tab distal end 72 of slidable push tab 66. Strain relief member 74 may be integral with (e.g., formed from the same material as slidable push tab 66 as part of the same manufacturing step) or attached to slidable push tab 66. Strain relief member 74 may relieve or dissipate stress that otherwise would be concentrated in push member 22 at slidable push tab distal end 72. Additionally, strain relief member 74 may provide radial stiffness to push member 22 to reduce or eliminate bending or kinking of push member 22 in response to axial forces being applied to slidable push grip 64 when the slidable push grip 64 is engaged with push member 22.

Strain relief member 74 defines a lumen 76 that extends from a proximal end of strain relief member 74 to a distal end of strain relief member 74. Lumen 76 may be coincident with lumen 68 of slidable push tab 66 (e.g., lumen 76 and lumen 68 may share a long axis parallel to the L-axis of FIG. 3). In examples in which strain relief member 74 is attached to slidable push tab 66, strain relief member 74 may be attached to slidable push tab 66 using any suitable mechanism, including, for example, an adhesive, ultrasonic welding, solvent casting, a friction fit, a mechanical interlock, or the like.

Figure 4:
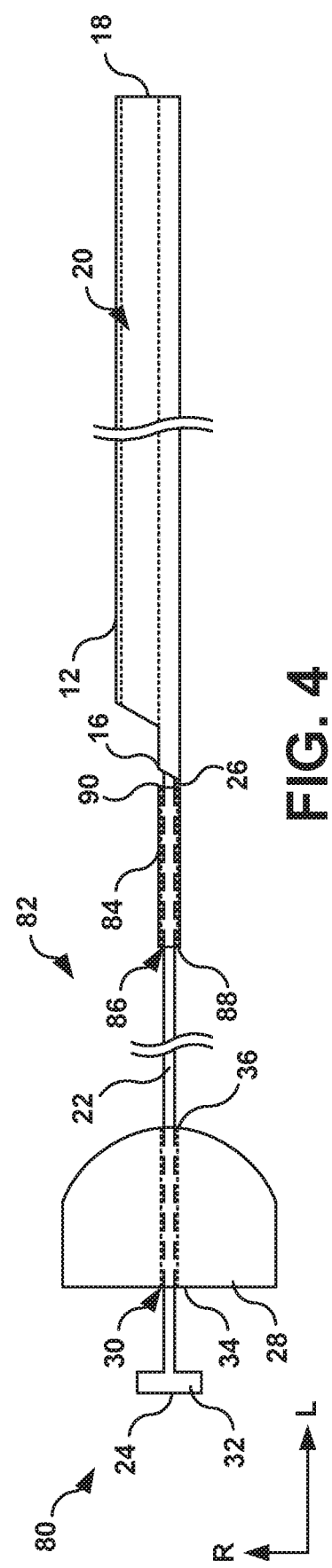
FIG. 4 is a conceptual side view illustrating an example catheter, which includes an elongate body, a push assembly including a push member and a slidable push grip, and a kink resistance sleeve.

FIG. 4 is a conceptual side view of another example catheter 80, which includes an elongate body 12, a push assembly 82 including a push member 22, a slidable push tab 28, and a kink resistance sleeve 84. Catheter 80 may be similar or substantially the same as catheter 10 of FIG. 1, aside from the differences described herein. For example, like catheter 10, catheter 80 includes elongate body 12, which extends from proximal end 16 to distal end and defines lumen 20. Catheter 80 also includes a push assembly 82, which, like catheter 10, includes a push member 22 that extends from proximal end 24 to distal end 26 and includes an optional proximal end stop 32. Distal end 26 of push member 22 is mechanically coupled to proximal end 16 of elongate body 12. Like push assembly 14 of FIG. 1, push assembly 82 of FIG. 4 also includes slidable push tab 28, which extends from a proximal end 34 to a distal end 36 and defines an aperture 30 though which push member 22 extends.

Push assembly 82 also includes a kink resistance sleeve 84. Kink resistance sleeve 84 is physically separate from slidable push tab 28. Kink resistance sleeve 84 extends from a kink resistance sleeve proximal end 88 to a kink resistance sleeve distal end 90 and defines a kink resistance sleeve aperture 86 that from kink resistance sleeve proximal end 88 to kink resistance sleeve distal end 90.

Kink resistance sleeve aperture 86 had a diameter or cross-sectional area that is larger than an outer diameter or cross-sectional area of push member 22, such that push member 22 may slide through kink resistance sleeve aperture 86. The diameter or cross-sectional area of kink resistance sleeve aperture 86 is sufficiently close to the outer diameter or cross-sectional area of push member 22 that kink resistance sleeve 84 provides structural support to push member 22. For example, kink resistance sleeve 84 may provide radial stiffness to push member 22 to reduce or eliminate bending or kinking of push member 82 as axial forces are applied to slidable push grip 28 when slidable push tab 28 is engaged with push member 22. In some examples, a single component may act as both a strain relief member 74 and a kink resistance member 84 and may be referred to as either a strain relief member or a kink resistance member. In other examples, a single catheter may include both a strain relief member 74 and a kink resistance member 84. In some such examples, a diameter or cross-sectional area of kink resistance sleeve aperture 86 may be larger than an outer diameter or cross-sectional area of strain relief member 74, such that a distal end of strain relief member 74 may be advanced into kink resistance sleeve aperture 86.

In examples in which kink resistance member 84 is physically separate from slidable push tab 28, kink resistance member 84 is movable along push member 22 separate from slidable push tab 28. This may allow kink resistance member 84 to be moved to a more distal location on push member 22, such as adjacent to an introducer sheath, a hub, or another place at which bending or kinking of push member 22 is likely as catheter 80 is being advanced into vasculature of a patient.

In some examples, kink resistance member 84 may be removable from around push member 22. For example, kink resistance member 84 may include a clamshell type configuration that snaps or clips around the perimeter of push member 22. As another example, kink resistance member 84 may be formed from a polymer that includes one or more portions of reduced structural integrity (e.g., perforations, thinner wall sections, or the like), to allow kink resistance member 84 to be removed from push member 22 by tearing kink resistance member 84 along the long axis of kink resistance member 84 (e.g., parallel to the L-axis of FIG. 4).

Figure 5:
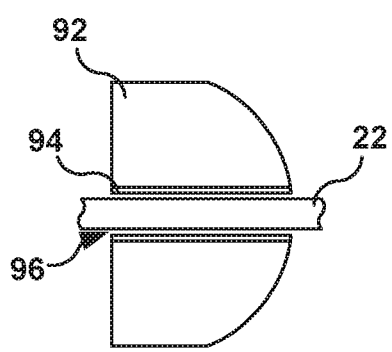
FIG. 5 is a conceptual cross-sectional view illustrating an example push member and an example slidable push grip.

In some examples, regardless of the configuration of the slidable push grip, a surface of the aperture in the slidable push grip through which push member 22 extends may include at least one engagement feature to facilitate engagement of the slidable push grip with the push member 22. For example, FIG. 5 is a conceptual cross-sectional diagram illustrating a portion of another example slidable push grip 92 and a portion of a push member 22. The cross-sectional diagram is taken along a longitudinal axis of push member 22. Push member 22 is the same as or substantially similar to push member 22 described with reference to FIG. 1. Slidable push grip 92 is illustrated similar to slidable push tab 28 of FIG. 1, but the principles described with reference to FIG. 5 are applicable to the other slidable push grips described herein.

Slidable push grip 92 includes engagement features that includes a surface feature 94 on the surface of slidable push grip 92 that defines slidable push grip aperture 96 through which push member 22 extends. Surface feature 94 may include any surface modification that increases grip between push member 22 and slidable push grip 92, e.g., compared to an unmodified slidable push grip 92. In some examples, surface feature 94 may include surface texturing. In addition to or instead of the texturing, surface feature 94 may include a coating, such as a coating of material that has a higher coefficient of friction with push member 22 than the untreated surface. For example, the coating may include a rubbery material, such as a medical grade silicone. By facilitating engagement of slidable push grip 92 with push member 22, surface feature 94 may improve force transmission from slidable push grip 92 to push member 22.

Figure 6:
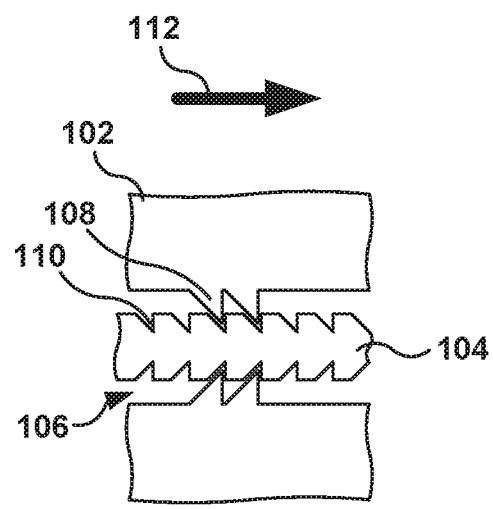
FIG. 6 is a conceptual cross-sectional view illustrating another example push member and another example slidable push grip.

In some examples, an outer surface (e.g., an outer circumferential surface) of the push member also may have at least one surface feature that facilitates engagement with the slidable push grip. For example, FIG. 6 is a conceptual cross-sectional diagram illustrating a portion of an example slidable push grip 102 and a portion of an example push member 104. The cross-sectional diagram is taken along a longitudinal axis of push member 104. In the example shown in FIG. 6, an inner surface (e.g., inner circumferential surface) of slidable push grip 102 includes a geometric pattern, which in the illustrated example, includes a plurality of teeth 108. Push member 104 includes an outer surface that defines a complementary geometric pattern, which, in the illustrated example, includes a plurality of depressions 110. Together, plurality of teeth 108 and plurality of depressions 110 act to facilitate engagement between push member 104 and slidable push grip 102.

For example, slidable push grip aperture 106 may be sized so that respective teeth of plurality of teeth 108 extend into respective depressions of plurality of depressions 110 in the absence of an applied radial force to slidable push grip 102. Plurality of teeth 108 and plurality of depressions 110 are shaped to allow proximal movement of slidable push grip 102 relative to push member 104, while not allowing substantial distal movement of slidable push grip 102 relative to push member 104 in response to the same given force. In this way, slidable push grip 102 may be engaged with push member 104 by applying a distally directed axial force parallel to arrow 112 and disengaged from push member 104 by applying a proximally directed axial force anti-parallel to arrow 112. This enables slidable push grip 102 to be repositioned to a more proximal position along push member 104 without transferring significant axial forces to push member 104 and facilitates transfer of axial forces in the distal direction form slidable push grip 102 to push member 104. Further, the combination of plurality of teeth 108 and plurality of depressions 110 may act like a ratcheting mechanism.

FIG. 6 illustrates one example of a geometric pattern on an inner surface of slidable push grip 102 and a complementary geometric pattern on an outer surface of push member 104. Other geometric patterns are also contemplated, such as a helical pattern that enables screwing of slidable push grip 102 into engagement with push member 104, other shapes of teeth and depressions, or the like. Additionally, in some examples, an inner surface of slidable push grip 102 may include a geometric pattern, such as teeth, and an outer surface of push member 104 may omit the complementary geometric pattern.

Figure 7:
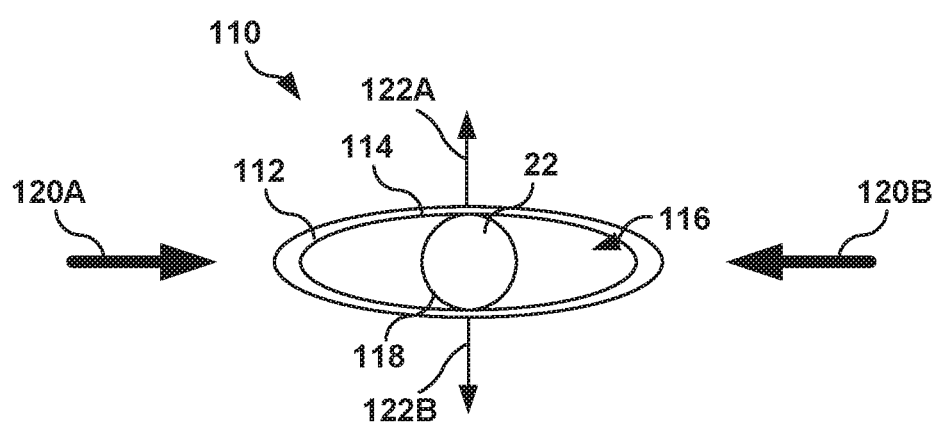
FIG. 7 is a conceptual cross-sectional view illustrating another example catheter including a push member and slidable push grip.

In many of the examples described above, the slidable push grip defaults to (e.g., is biased to) a disengaged state with the push member in the absence of an applied radially inward force to the slidable push grip. In other examples, a slidable push grip may default to (e.g., be biased to) an engaged state with a push member in the absence of an applied radially inward force to the slidable push grip. For example, FIG. 7 is a conceptual cross-sectional view illustrating another example catheter 110 that includes a push member 22 and a slidable push grip 112. Slidable push grip 112 defines a slidable push grip aperture 116 that extends from a proximal end to a distal end of slidable push grip 112. Push member 22 extends within slidable push grip aperture 116.

In the example of FIG. 7, slidable push grip 112 defines an elliptical or oval cross-sectional shape in a plane transverse to the longitudinal axis of push member 22. The size of slidable push grip aperture 116 is selected so an inner surface 114 of slidable push grip 112 contacts and engages with an outer surface 118 of push member 22. In this way, slidable push grip 112 defaults to an engaged state with push member 22 in the absence of an applied radially inward force to slidable push grip 112. To disengage slidable push grip 112 from push member 22, a clinician may apply a radially inward force (indicated by arrows 120A and 120B), which results in deformation of slidable push grip 112 away from push member 22 in the direction indicated by arrows 122A and 122B.

In some examples, a slidable push grip may include a locking feature for maintaining the slidable push grip in an engaged state, a disengaged state, or either an engaged state or a disengaged state.

Figure 8:
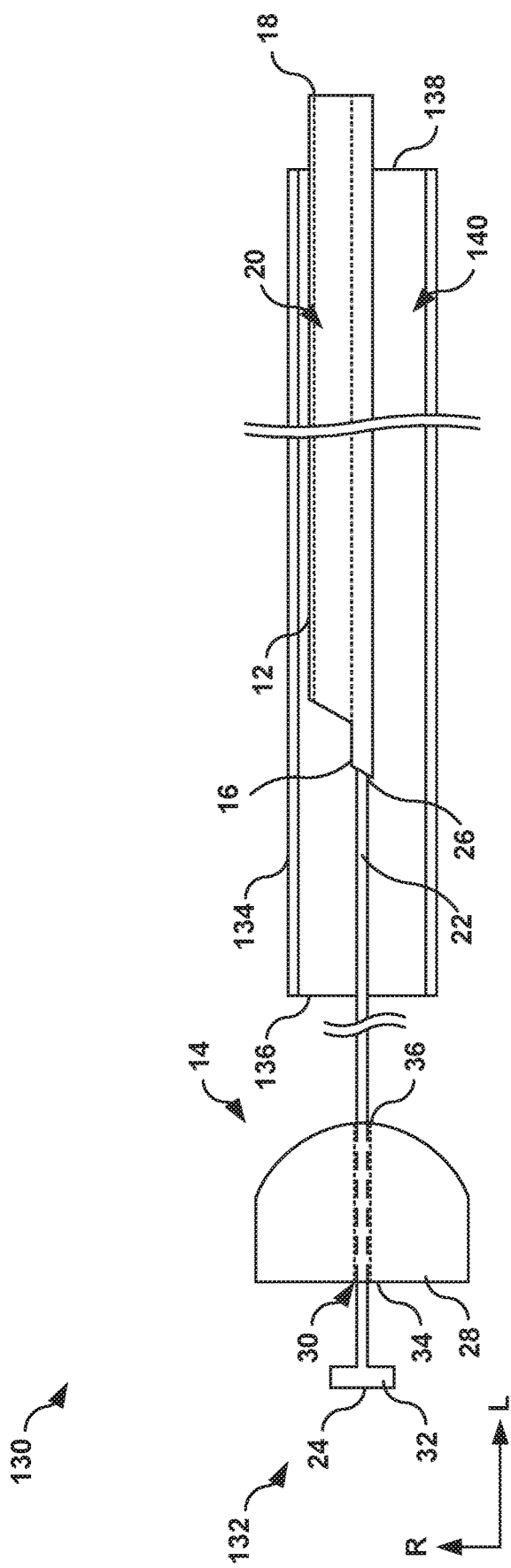
FIG. 8 is a conceptual cross-sectional view illustrating an example catheter system including a guide extension catheter and an outer catheter.

Although FIGS. 1-7 have described and illustrated catheters alone, in some examples, the catheters described herein may be used as part of a catheter system that includes at least one other component. For example, the catheters described herein may be used as a guide extension catheter for extending an effective length of an outer catheter to access more distal locations within vasculature of a patient. FIG. 8 is a conceptual cross-sectional view illustrating an example catheter system 130 including a guide extension catheter 132 and an outer catheter 122. Although FIG. 8 illustrates guide extension catheter 132 as being substantially identical to catheter 10 of FIG. 1, guide extension catheter 132 may include any of the catheters described herein.

As shown in FIG. 8, outer catheter 134 extends from an outer catheter proximal end 136 to an outer catheter distal end 138 and defines an outer catheter lumen 140 extending from outer catheter proximal end 136 to outer catheter distal end 138. In some examples, catheter system 130 may include other components that are not shown in FIG. 8 for purposes of clarity. For example, outer catheter 134 may be introduced into vasculature of a patient through an introducer, which, in some examples, may include a hub at a proximal end of the introducer. As another example, a guidewire may extend through at least part of a length of outer catheter lumen 140 and extend proximally from outer catheter proximal end 136.

Guide extension catheter 132 defines an outer diameter or cross-sectional area that is less than a diameter or cross-sectional area of outer catheter lumen 140. As shown in FIG. 8, a clinician may insert a distal end 18 of elongate body 12 of guide extension catheter 132 into outer catheter lumen 140 at outer catheter proximal end 136 and advance guide extension catheter 132 distally through outer catheter lumen 140 by applying a distally directed axial force (along direction L) to slidable push tab 28 while slidable push tab 28 is engaged with push member 22. Push member 22 transmits the distally directed axial force to elongate body 12, which results in distal movement of guide extension catheter 132.

Guide extension catheter 132 defines a length greater than a length of outer catheter 134, such that at least a distal end 18 of elongate body 12, and up to an entire length of elongate body 12 can be advanced to extend distally from outer catheter distal end 138 while at least part of push member 22 extends proximally from outer catheter proximal end 136. For example, push member 22 may have a length of about 125 cm and elongate body 12 may have a length of about 25 cm. In this way, outer catheter 134 may be introduced in vasculature of a patient and advanced to near (but proximal to) a treatment site. Guide extension catheter 132 may be introduced in outer catheter lumen 140 and advanced through outer catheter lumen 140 to and out of outer catheter distal end 138. Push member 22 has a lower profile than elongate body 12, and, as a result, may occupy less space within outer catheter lumen 140 than elongate body 12. Thus, push assembly 14, including one or more slidable push member tab 28, strain relief member 74, or kink resistance sleeve 84, may facilitate pushability of guide extension catheter 132 through outer catheter 134 and/or through vasculature of a patient, while still enabling relatively large medical devices to be introduced through outer catheter lumen 140 to reach lumen 20 of guide extension catheter 132. For example, slidable push member tab 28, strain relief member 74, and/or kink resistance sleeve 84 may facilitate axial pushability of push member 22 while enabling a cross-sectional area of push member 22 in a plane transverse to the longitudinal axis of push member 22 to be reduced. In this way, guide extension catheter 132 may act as an extension for outer catheter 134. In some examples, guide extension catheter 132 may be used to traverse tortuous vasculature that outer catheter 134 is not sufficiently flexible to traverse or may be advanced through calcification within a body vessel.

Figure 9:
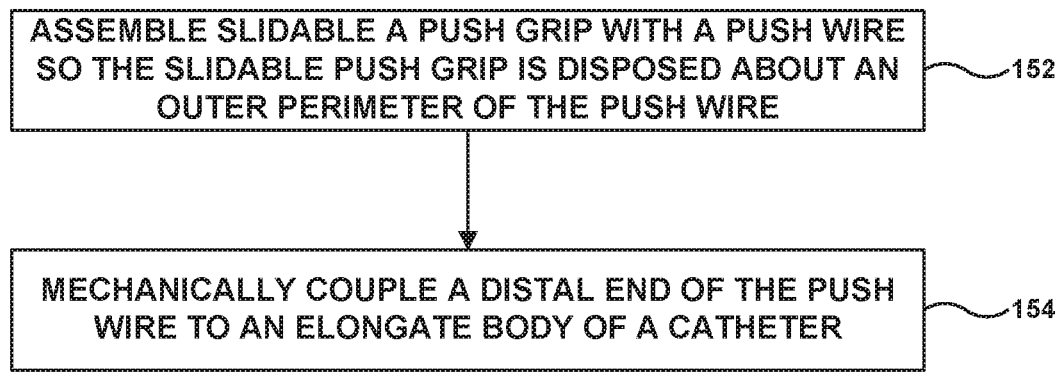
FIG. 9 is a flow diagram illustrating an example method for manufacturing an example catheter, which includes an elongate body and a push assembly including a push member and a slidable push grip.

FIG. 9 is a flow diagram illustrating an example method for manufacturing an example catheter, which includes an elongate body and a push assembly including a push member and a slidable push grip. The technique of FIG. 9 will be described with reference to catheter 10 of FIG. 1. A person having ordinary skill in the art will understand that the technique of FIG. 9 may be applied to manufacture other catheters described herein, and that catheters described herein may be manufactured using other techniques.

The technique of FIG. 9 includes assembling a slidable push grip 28 with a push member 22 so slidable push grip 28 is disposed about an outer perimeter of push member 22 (152). For example, a distal end 26 of push member 22 may be inserted into slidable push tab aperture 30 at a proximal end 34 of slidable push grip 28 and advanced through slidable push tab aperture 30 until distal end 26 of push member 22 extends out distal end 36 of slidable push grip 28. Slidable push grip 28 surrounds a perimeter, e.g., circumference, of push member 22.

The technique of FIG. 9 also includes mechanically coupling a distal end 26 of push member 22 to elongate body 12 of catheter 10 (154). For example, a distal portion of push member 22 including distal end 26 may be embedded in the polymer from which elongate body 12 is at least partially formed or adhered to elongate body 12.

Figure 10:
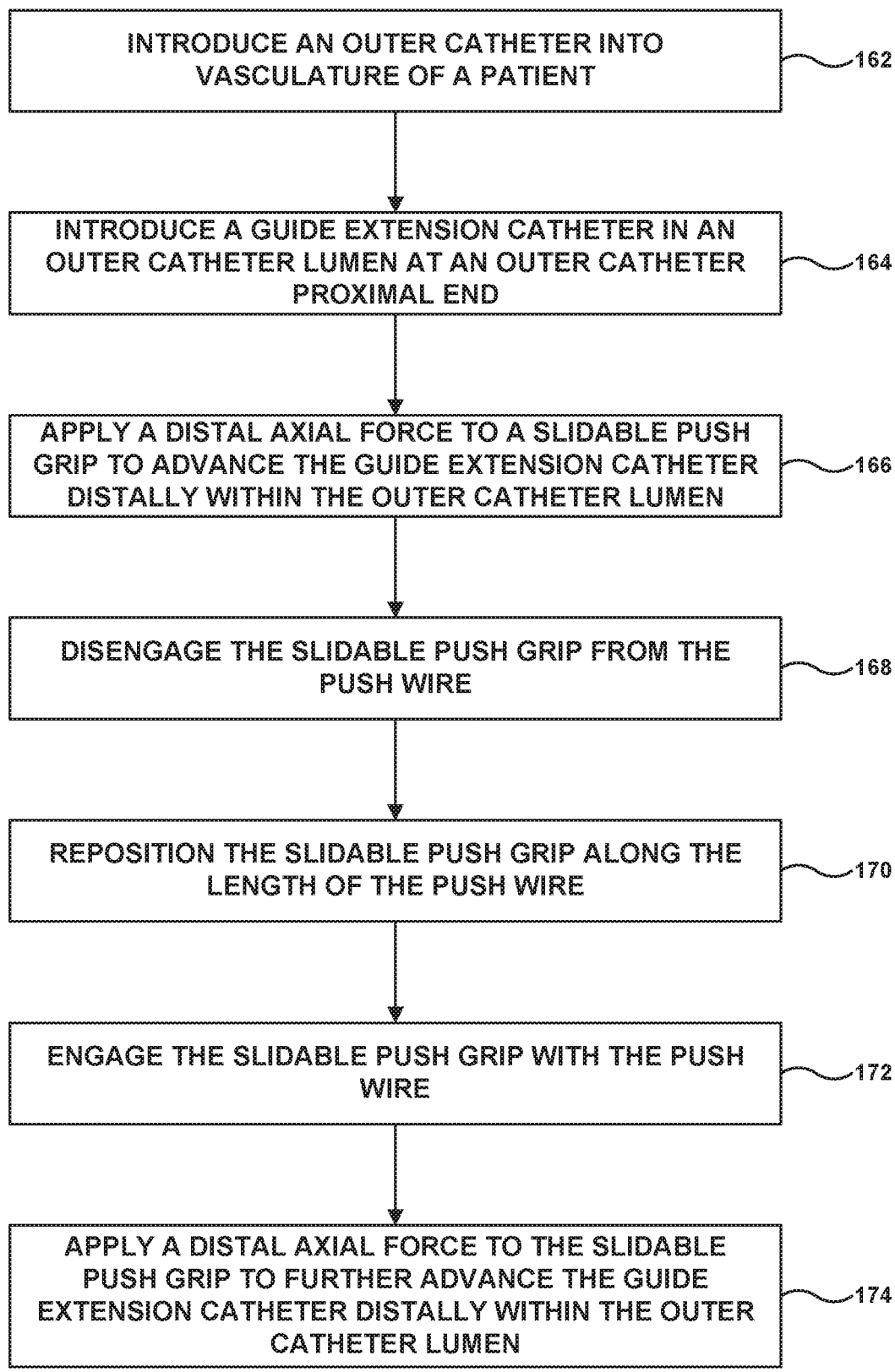
FIG. 10 is a flow diagram illustrating an example method for introducing an example catheter, which includes an elongate body and a push assembly including a push member and a slidable push grip, in vasculature of a patient.

FIG. 10 is a flow diagram illustrating an example method for introducing an example catheter, which includes an elongate body and a push assembly including a push member and a slidable push grip, into vasculature of a patient. The technique of FIG. 10 will be described with reference to catheter system 130 of FIG. 8. A person having ordinary skill in the art will understand that the technique of FIG. 10 may be applied using other catheters described herein, and that catheters described herein may be used in other techniques.

The technique of FIG. 10 includes introducing outer catheter 134 into vasculature of a patient (162). For example, a clinician may introduce outer catheter 134 into vasculature of a patient through an introducer, which, in some examples, may include a hub at a proximal end of the introducer. In particular, in some examples, outer catheter distal end 138 may be introduced into an introducer, and a clinician may apply a distally directed axial force to outer catheter 134 directly to advance outer catheter 134 within vasculature of a patient. In some examples, a clinician may position a guidewire in the vasculature and guide outer catheter 134 through the vasculature over the guidewire. In some examples, outer catheter 134 may be used in a coronary procedure. The clinician may introduce outer catheter 134 into vasculature of the patient and advance outer catheter 134 toward the coronary artery. However, in some example, outer catheter 134 and any guidewire used may not extend sufficiently far or be sufficiently maneuverable to enter the coronary artery or allow introduction of other medical devices into the coronary artery.

Once outer catheter 134 is introduced in vasculature of a patient (162) and positioned at a desired location, the clinician may introduce guide extension catheter 132 in outer catheter lumen 140 at outer catheter proximal end 136 (164). The clinician then may apply a distally directed axial force to slidable push grip 28 to advance guide extension catheter 132 distally within outer catheter lumen 140 (166). To advance guide extension catheter 132 distally within outer catheter lumen 140, the clinician may apply the distally directed axial force while slidable push grip 28 is in the engaged state with push member 22. For example, the clinician may grip slidable push grip 28 and cause slidable push grip 28 to engage push member 22, e.g., by applying a radially inward force to slidable push grip 28. The clinician then may apply the distally directed axial force to slidable push grip 28, which transmits the force to push member 22, and, ultimately, elongate body 12. The clinician may apply the distally directed axial force for a desired time and distal axial displacement of guide extension catheter 132.

The clinician then may disengage slidable push grip 28 from push member 22 (168), e.g., by removing the radially inward force form slidable push grip 28 or actuating a locking feature of slidable push grip 28. The clinician then may reposition slidable push grip 28 along the length of push member 22 (170) and reengage slidable push grip 28 with push member 22 (172). For example, the clinician may move slidable push grip 28 proximally along push member 22 a desired distance to a new axial location. For example, the clinician may move slidable push grip 28 proximally along push member 22 in response to additional length of push member 22 being introduced into outer catheter 134, e.g., in response to slidable push grip 28 approaching proximal end 136 of outer catheter 134. The clinician then may engage slidable push grip 28 with push member 22, e.g., by applying a radially inward force to slidable push grip 28.

Once slidable push grip 28 is reengaged with push member 22, the clinician may apply a distally directed axial force to slidable push grip 28 to further advance guide extension catheter 132 distally through outer catheter lumen 140 (174). The clinician may repeat steps (168)-(174) as many times as required or desired to advance guide extension catheter 132 to a desired position relative to outer catheter 134. For example, the clinician may repeat steps (168)-(174) until substantially all of elongate body 12 extends distally out of outer catheter lumen 140, e.g., aside from a selected portion of elongate body 12 near elongate body proximal end 16. For example, the selected portion of elongate body 12 may extend into the coronary artery to extend an effective length of outer catheter 134 and facilitate introduction of other medical devices into the coronary artery. Although not shown in FIG. 10, the clinician may then advance a medical device, therapeutic agent, or the like through outer catheter lumen 140 and elongate body lumen 20 to a treatment site near elongate body distal end 18.

Various examples have been described. Any combination of the described systems, devices, operations, or functions is contemplated. These and other examples are within the scope of the following claims.

What is claimed is:

1. A guide extension catheter comprising:
   an elongate body extending from a proximal end to a distal end and defining a lumen;
   a push member mechanically coupled to the proximal end of the elongate body, wherein the push member has a lower profile than the elongate body, and wherein the elongate body and the push member are configured to be received in an outer catheter; and a slidable push grip disposed about an outer perimeter of the push member, wherein the slidable push grip is controllably engageable with the push member, wherein, when the slidable push grip is in an engaged state with the push member and the elongate body is received in the outer catheter, an axial force applied to the slidable push grip translates the push member to relative to the outer catheter to translate the elongate body relative to the outer catheter, wherein, when the slidable push grip is in a disengaged state with the push member, the slidable push grip is movable axially in at least one direction along a length of the push member and relative to the push member, and wherein the slidable push grip is configured to be in the engaged state with the push member at a plurality of locations along the length of the push member.

2. The guide extension catheter of claim 1, wherein the push member comprises a proximal end stop at or near a proximal end of the push member, and wherein the proximal end stop is configured to prevent the slidable push grip from being removed off the proximal end of the push member.

3. The guide extension catheter of claim 1, wherein the slidable push grip surrounds the outer perimeter of the push member so the slidable push grip is not radially removable from the push member.

4. The guide extension catheter of claim 1, wherein the slidable push grip comprises at least one engagement feature on an inner surface of the slidable push grip, and wherein the at least one engagement feature is configured to increase engagement of the inner surface of the slidable push grip with the push member.

5. The guide extension catheter of claim 4, wherein the at least one engagement feature comprises at least one of a coating applied to the inner surface of the slidable push grip, wherein the coating increases a coefficient of friction with the push member; a texture on the inner surface of the slidable push grip, wherein the texture increases a coefficient of friction with the push member; or a geometric pattern formed in the inner surface of the push member.

6. The guide extension catheter of claim 5, wherein the at least one engagement feature comprises the geometric pattern formed in the inner surface, and wherein an outer surface of the push member comprises a complementary pattern.

7. The guide extension catheter of claim 1, wherein the slidable push grip further comprises a locking feature configured to controllably maintain the slidable push grip in the engaged state or the disengaged state.

8. The guide extension catheter of claim 1, further comprising a kink resistance sleeve disposed about the outer perimeter of the push member, wherein the kink resistance sleeve is configured to reduce radial bending or kinking of the push member.

9. The guide extension catheter of claim 1, further comprising a strain relief member attached to or integral with the slidable push grip and extending distally from a distal end of the slidable push grip.

10. The guide extension catheter of claim 1, wherein the slidable push grip is configured to default to the disengaged state and transition to the engaged state in response to a radially inward force being applied to the slidable push grip.

11. The guide extension catheter of claim 1, wherein the slidable push grip is configured to default to the engaged state and disengage the push member in response to a radially inward force being applied to the slidable push grip.

12. A catheter system comprising:
an outer catheter extending from an outer catheter proximal end to an outer catheter distal end and defining an outer catheter lumen; and
a guide extension catheter (GEC) comprising:
an elongate body extending from a proximal end to a distal end and defining a lumen;
a push member mechanically coupled to the proximal end of the elongate body, wherein the push member has a lower profile than the elongate body, and wherein the elongate body and the push member are configured to be received in the outer catheter lumen; and
a slidable push grip disposed about an outer perimeter of the push member, wherein the slidable push grip is controllably engageable with the push member,
wherein, when the slidable push grip is in an engaged state with the push member, and the elongate body is received in the outer catheter, an axial force applied to the slidable push grip translates the push member relative to the outer catheter to translate the elongate body relative to the outer catheter,
wherein, when the slidable push grip is in a disengaged state with the push member, the slidable push grip is movable axially in at least one direction along a length of the push member and relative to the push member, and
wherein the slidable push grip is configured to be in the engaged state with the push member at a plurality of locations along the length of the push member.

13. The catheter system of claim 12, wherein the elongate body of the guide extension catheter defines a maximum outer diameter that is less than a diameter of the outer catheter lumen.

14. The catheter system of claim 12, wherein the guide extension catheter defines a length that is greater than a length of the outer catheter.

15. The catheter system of claim 12, wherein the push member comprises a proximal end stop at or near a proximal end of the push member, and wherein the proximal end stop is configured to prevent the slidable push grip from being removed off the proximal end of the push member.

16. The catheter system of claim 12, wherein the slidable push grip surrounds the outer perimeter of the push member so the slidable push grip is not radially removable from the push member.

17. The catheter system of claim 12, wherein the slidable push grip comprises at least one engagement feature on an inner surface of the slidable push grip, wherein the at least one engagement feature is configured to increase engagement of the inner surface of the slidable push grip with the push member, and wherein the at least one engagement feature comprises at least one of a coating applied to the inner surface of the slidable push grip, a texture on the inner surface of the slidable push grip, or a geometric pattern formed in the inner surface of the push member.

18. The catheter system of claim 17, wherein the at least one engagement feature comprises the geometric pattern formed in the inner surface, and wherein an outer surface of the push member comprises a complementary pattern.

19. The catheter system of claim 12, wherein the slidable push grip further comprises a locking feature configured to controllably maintain the slidable push grip in the engaged state or the disengaged state.

20. The catheter system of claim 12, further comprising a kink resistance sleeve disposed about the outer perimeter of the push member, wherein the kink resistance sleeve is configured to reduce radial bending or kinking of the push member.

21. The catheter system of claim 12, further comprising a strain relief member attached to or integral with the slidable push grip and extending distally from a distal end of the slidable push grip.

22. A method comprising:
- introducing an outer catheter in vasculature of a patient, wherein the outer catheter extends from an outer catheter proximal end to an outer catheter distal end and defines an outer catheter lumen;
- introducing a guide extension catheter in the outer catheter lumen at the outer catheter proximal end, wherein the guide extension catheter comprises an elongate body extending from a proximal end to a distal end and defining a guide extension catheter lumen, a push member having a lower profile than the elongate body mechanically coupled to the proximal end, and a slidable push grip disposed about an outer perimeter of the push member, wherein the slidable push grip is controllably engageable with the push member, wherein, when the slidable push grip is in an engaged state with the push member and the elongate body is received in the outer catheter lumen, an axial force applied to the slidable push grip translates the push member relative to the outer catheter to translate the elongate body relative to the outer catheter, and wherein, when the slidable push grip is in a disengaged state with the push member, the slidable push grip is movable axially in at least one direction along a length of the push member and relative to the push member;
- while the slidable push grip is in the engaged state with the push member, applying a distal axial force to the slidable push grip to advance the guide extension catheter distally within the outer catheter lumen;
- disengaging the slidable push grip from the push member;
- repositioning the slidable push grip along the length of the push member;
- after repositioning the slidable push grip along the length of the push member, engaging the slidable push grip with the push member; and
- while the slidable push grip is in the engaged state with the push member, applying a distal axial force to the slidable push grip to further advance the guide extension catheter distally through the outer catheter lumen.

* * * * *